(12) United States Patent
    Picone

(10) Patent No.:     US 12,611,088 B1
(45) Date of Patent:     Apr. 28, 2026

(54) DISPOSABLE ENDOSCOPE CAMERA

(71) Applicant: Eric Picone, Huntersville, NC (US)

(72) Inventor: Eric Picone, Huntersville, NC (US)

( * ) Notice: Subject to any disclaimer, the term of this patent is extended or adjusted under 35 U.S.C. 154(b) by 467 days.

(21) Appl. No.: 18/142,074

(22) Filed: May 2, 2023

(51) Int. Cl.
    *A61B 1/07*     (2006.01)
    *A61B 1/00*     (2006.01)
    *A61B 1/015*    (2006.01)
    *A61B 1/018*    (2006.01)

(52) U.S. Cl.
    CPC ...... *A61B 1/00103* (2013.01); *A61B 1/00105* (2013.01); *A61B 1/00117* (2013.01); *A61B 1/00126* (2013.01); *A61B 1/015* (2013.01); *A61B 1/018* (2013.01); *A61B 1/00137* (2013.01); *A61B 1/07* (2013.01)

(58) Field of Classification Search
    CPC ....... A61B 1/015; A61B 1/00105; A61B 1/07; A61B 1/00117; A61B 1/00126; A61B 1/00103
    See application file for complete search history.

(56)              References Cited

U.S. PATENT DOCUMENTS 5,633,675  A  *  5/1997  Danna .................. A61B 1/0623
                                              600/129
8,928,746  B1     1/2015  Stevrin

| | | | |
|---|---|---|---|
| D829,325 | S | 9/2018 | Frenkler |
| 10,080,486 | B2 | 9/2018 | Levy |
| 10,258,222 | B2 | 4/2019 | Levin |
| 2011/0184244 | A1* | 7/2011 | Kagaya .............. A61B 1/00117 600/182 |
| 2012/0004503 | A1* | 1/2012 | Kawaura ........... A61B 1/00128 600/104 |
| 2017/0354323 | A1* | 12/2017 | Yajima .................... A61B 1/07 |
| 2019/0183324 | A1 | 6/2019 | Costin |
| 2021/0113068 | A1* | 4/2021 | Shin ..................... A61B 1/0055 |
| 2021/0204799 | A1 | 7/2021 | Magno |
| 2021/0228064 | A1 | 7/2021 | Sorensen |
| 2021/0338045 | A1 | 11/2021 | Crowley |
| 2022/0000341 | A1 | 1/2022 | Zhang |
| 2022/0210298 | A1 | 6/2022 | Yan |
| 2023/0371793 | A1* | 11/2023 | Magno .............. A61B 1/00142 |
| 2024/0138655 | A1* | 5/2024 | Kasai ................... A61B 1/0011 |
| 2024/0298880 | A1* | 9/2024 | Aiba ................... G02B 6/3821 |

\* cited by examiner

*Primary Examiner* — Michael J Carey
*Assistant Examiner* — Olivia Grace Starkey
(74) *Attorney, Agent, or Firm* — Kyle A. Fletcher, Esq.

(57)                ABSTRACT

The disposable endoscope camera is a disposable structure. The disposable endoscope is a catheter. The disposable endoscope is adapted for use with a patient. The disposable endoscope is configured for a single use. The disposable endoscope includes a disposable catheter cable structure, a disposable catheter terminating structure, a permanent catheter terminal, and a plurality of fiber optic cable transfer brackets. The disposable endoscope is a fiber optic device that: a) captures electromagnetic radiation from within a field of view; and, b) transmits the captured electromagnetic radiation to a medical device that converts the processed electromagnetic radiation into an image.

16 Claims, 6 Drawing Sheets

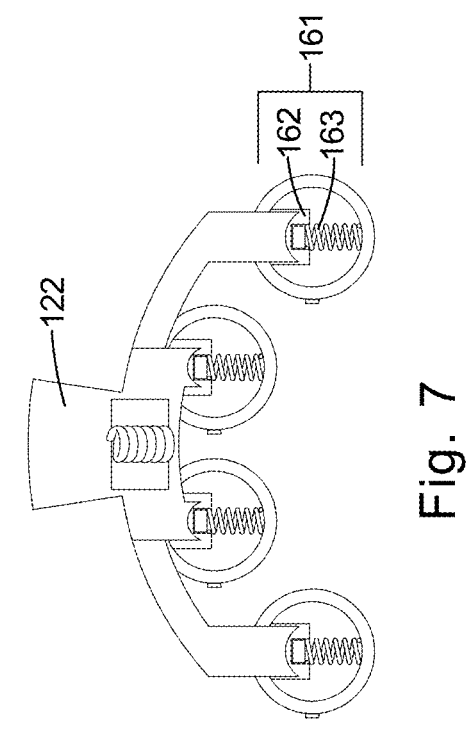
Fig. 7
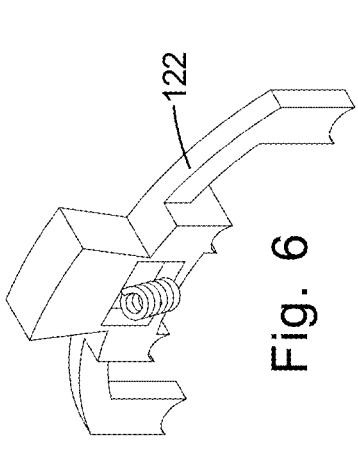
Fig. 6
Fig. 5
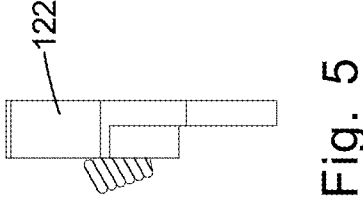
Fig. 4
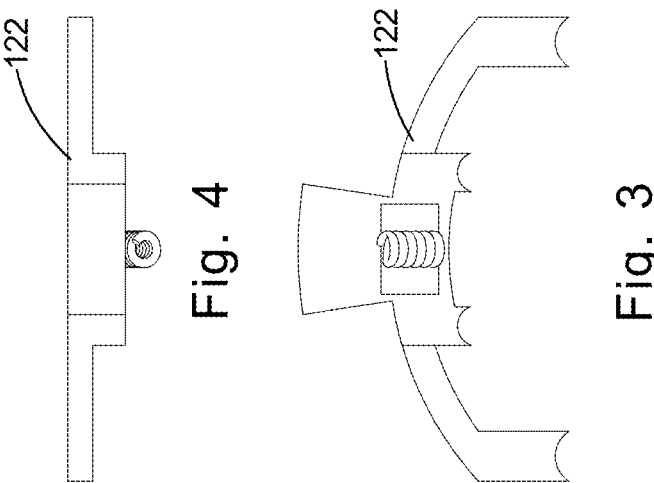
Fig. 3

DISPOSABLE ENDOSCOPE CAMERA

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the operational features of endoscopes. (A61B1/00042)

SUMMARY OF INVENTION

The disposable endoscope is a disposable structure. The disposable endoscope is a catheter. The disposable endoscope is adapted for use with a patient. The disposable endoscope is configured for a single use. The disposable endoscope comprises a disposable catheter cable structure, a disposable catheter terminating structure, a permanent catheter terminal, and a plurality of fiber optic cable transfer brackets.

The disposable catheter cable structure is a fiber optic device that: a) generates a field of illumination within a patient; b) captures electromagnetic radiation from within a field of view; and, c) transmits the electromagnetic radiation to the disposable catheter terminating structure. The disposable catheter terminating structure is a signal transfer structure. The disposable catheter terminating structure: a) receives the electromagnetic radiation transmitted by the disposable catheter cable structure; and, b) transfers the received electromagnetic radiation to the permanent catheter terminal. The permanent catheter terminal subsequently transfers the received the electromagnetic radiation to a medical device that converts the processed electromagnetic radiation into an image. The plurality of fiber optic cable transfer brackets transfers the exchange of electromagnetic radiation between the disposable catheter cable structure, the disposable catheter terminating structure, and the permanent catheter terminal.

These together with additional objects, features and advantages of the disposable endoscope will be readily apparent to those of ordinary skill in the art upon reading the following detailed description of the presently preferred, but nonetheless illustrative, embodiments when taken in conjunction with the accompanying drawings.

In this respect, before explaining the current embodiments of the disposable endoscope in detail, it is to be understood that the disposable endoscope is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the disposable endoscope.

It is therefore important that the claims be regarded as including such equivalent construction insofar as they do not depart from the spirit and scope of the disposable endoscope. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

FIG. 3 is a detail view of an embodiment of the disclosure.

FIG. 4 is a detail view of an embodiment of the disclosure.

FIG. 5 is a detail view of an embodiment of the disclosure.

FIG. 6 is a detail view of an embodiment of the disclosure.

FIG. 7 is a detail view of an embodiment of the disclosure.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Figures 1, 2:
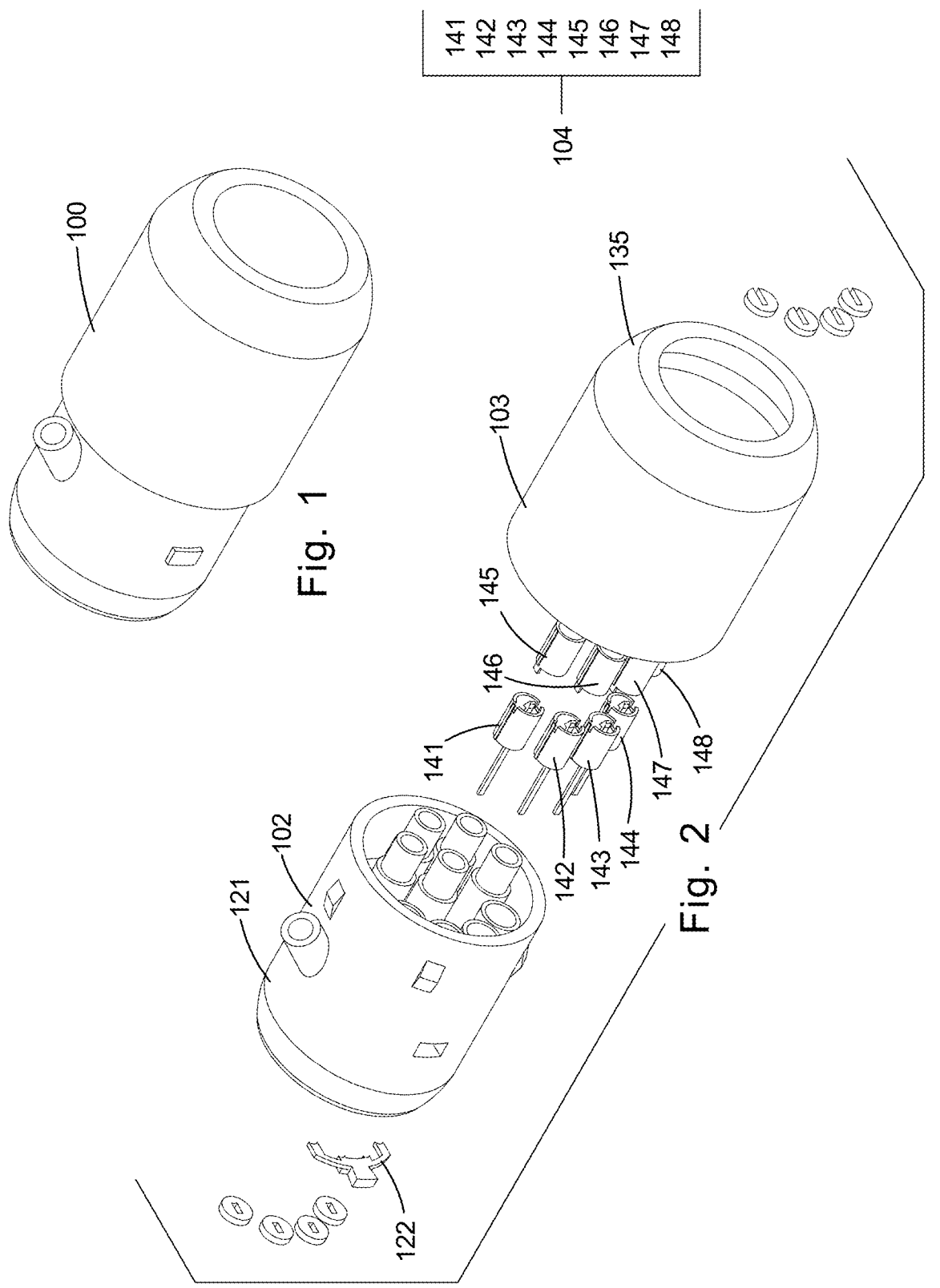
FIG. 1 is a perspective view of an embodiment of the disclosure.
FIG. 2 is an exploded view of an embodiment of the disclosure.
Figures 8, 9, 10, 11, 12, 13, 14, 15:
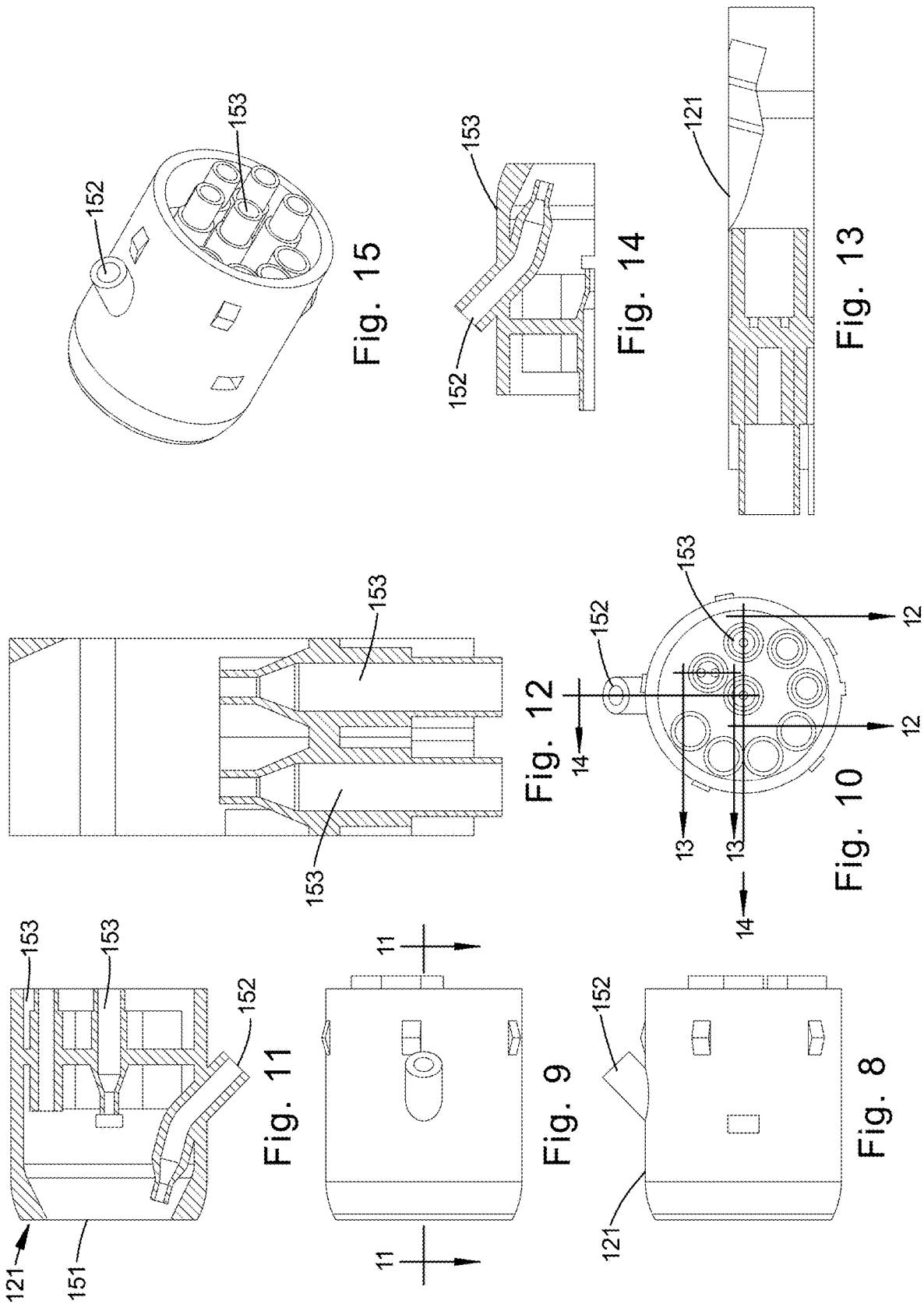
FIG. 8 is a detail view of an embodiment of the disclosure.
FIG. 9 is a detail view of an embodiment of the disclosure.
FIG. 10 is a detail view of an embodiment of the disclosure.
FIG. 11 is a detail view of an embodiment of the disclosure.
FIG. 12 is a detail view of an embodiment of the disclosure.
FIG. 13 is a detail view of an embodiment of the disclosure.
FIG. 14 is a detail view of an embodiment of the disclosure.
FIG. 15 is a detail view of an embodiment of the disclosure.
Figures 16, 17, 18, 19, 20:
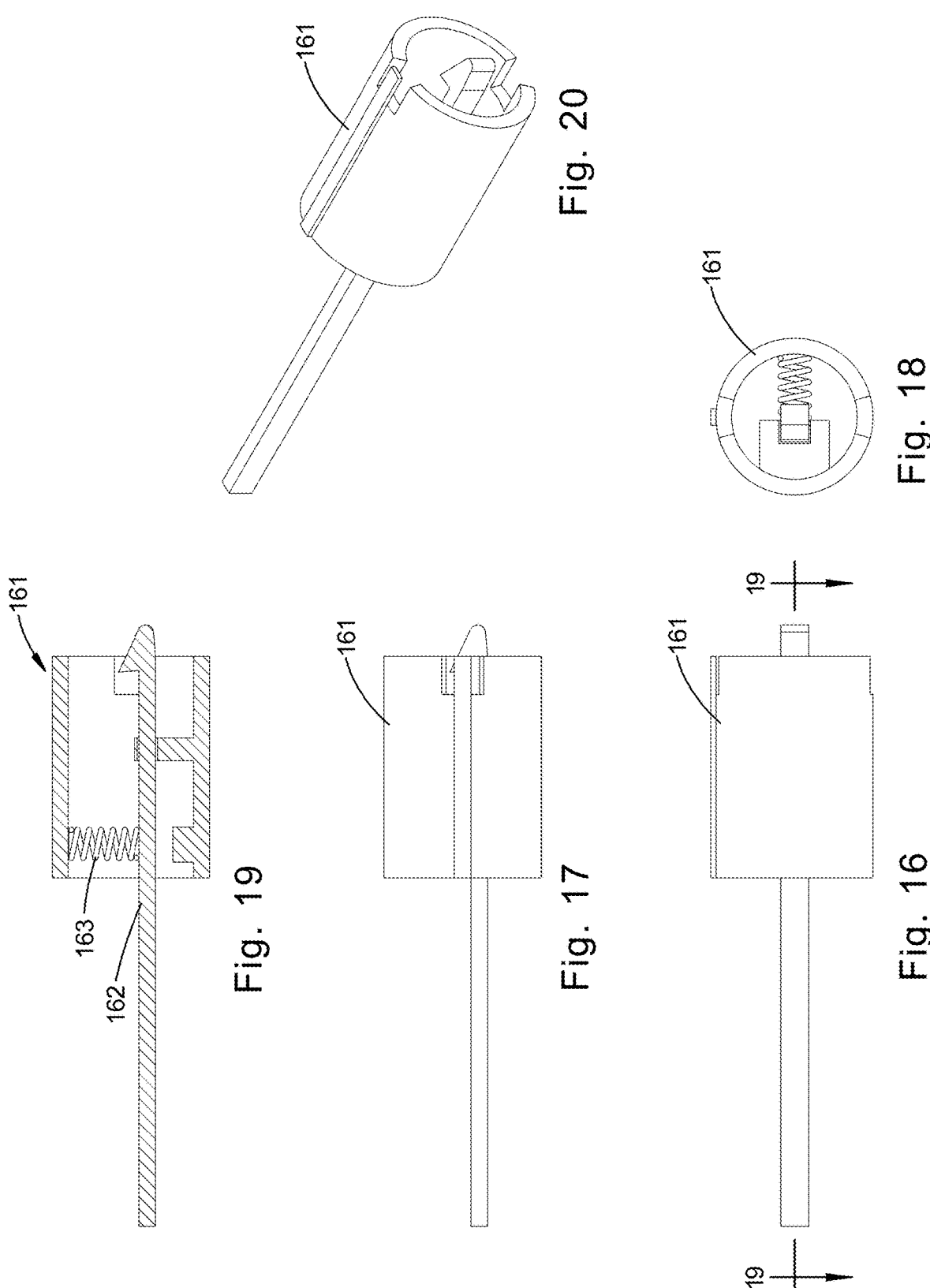
FIG. 16 is a detail view of an embodiment of the disclosure.
FIG. 17 is a detail view of an embodiment of the disclosure.
FIG. 18 is a detail view of an embodiment of the disclosure.
FIG. 19 is a detail view of an embodiment of the disclosure.
FIG. 20 is a detail view of an embodiment of the disclosure.
Figure 21:
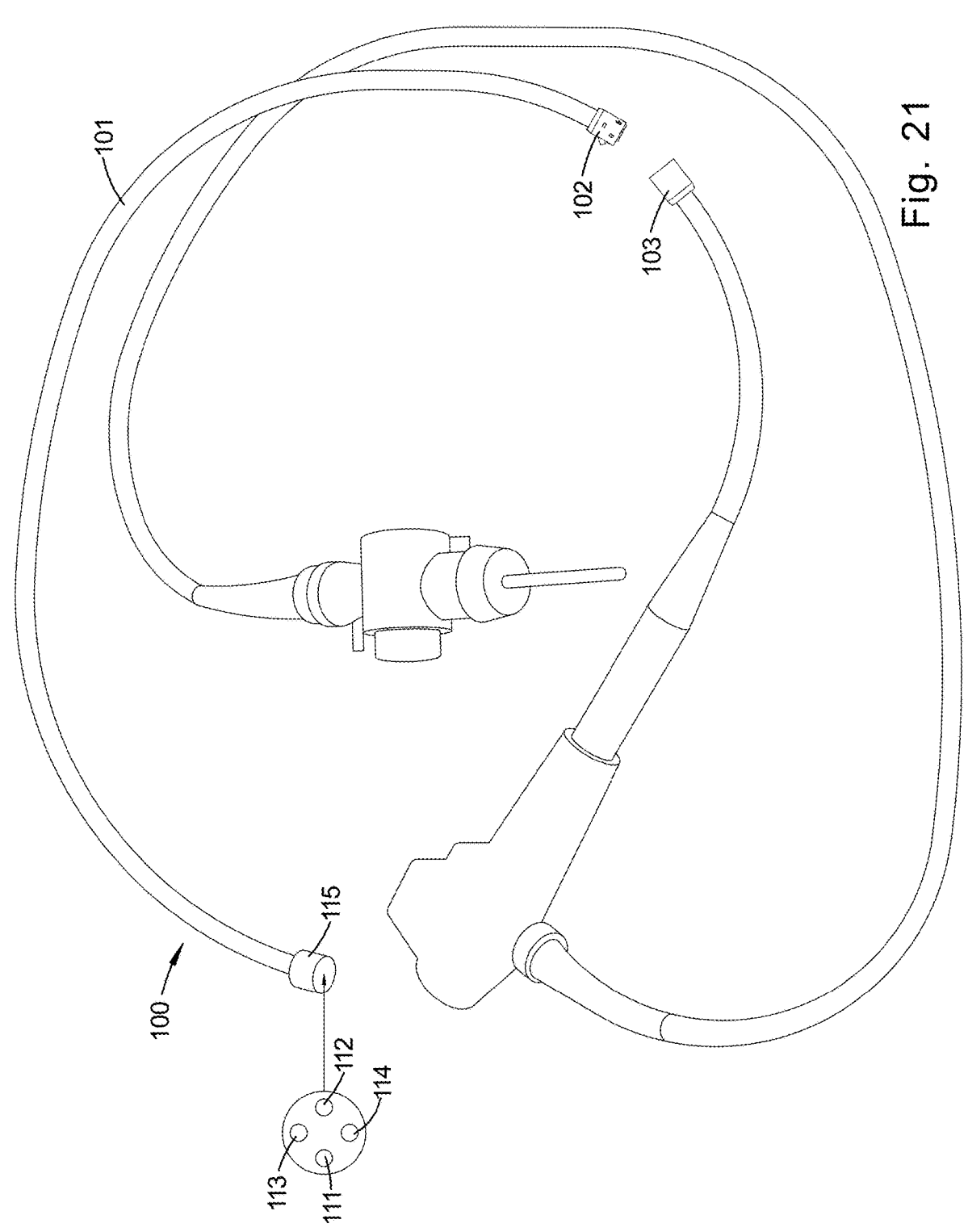
FIG. 21 is an in-use view of an embodiment of the disclosure.
Figures 22, 23:
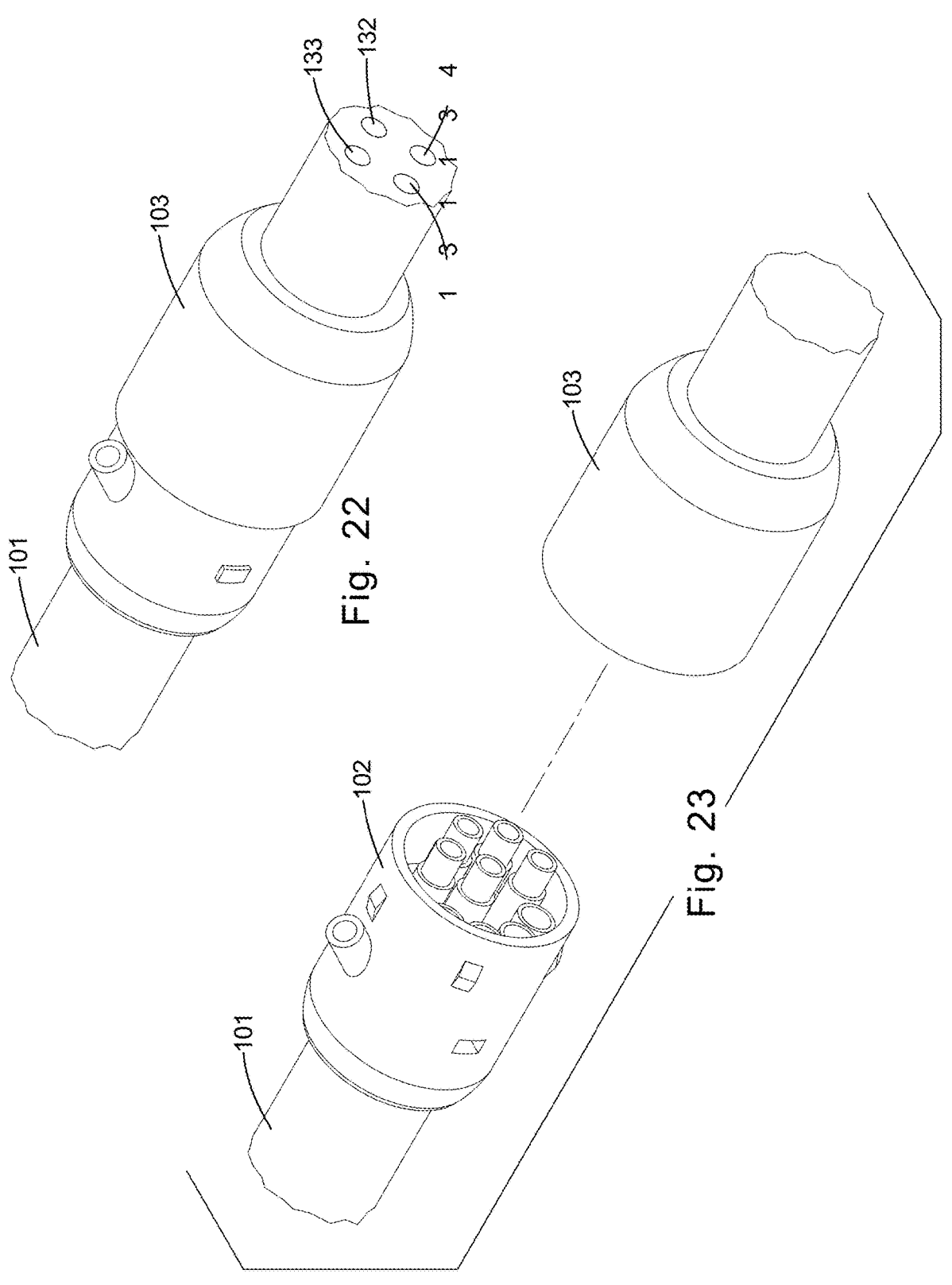
FIG. 22 is an in-use view of an embodiment of the disclosure.
FIG. 23 is an in-use view of an embodiment of the disclosure.

Detailed reference will now be made to one or more potential embodiments of the disclosure, which are illustrated in FIGS. 1 through 23.

The disposable endoscope 100 (hereinafter invention) is a disposable structure. The invention 100 is a catheter. The invention 100 is adapted for use with a patient. The invention 100 is configured for a single use. The invention 100 comprises a disposable catheter cable structure 101, a disposable catheter terminating structure 102, a permanent catheter terminal 103, and a plurality of fiber optic cable transfer brackets 104.

The disposable catheter cable structure 101 is a fiber optic device that: a) generates a field of illumination within a patient; b) captures electromagnetic radiation from within a field of view; and, c) transmits the electromagnetic radiation to the disposable catheter terminating structure 102. The disposable catheter terminating structure 102 is a signal transfer structure. The disposable catheter terminating structure 102: a) receives the electromagnetic radiation transmitted by the disposable catheter cable structure 101; and, b) transfers the received electromagnetic radiation to the permanent catheter terminal 103. The permanent catheter terminal 103 subsequently transfers the received the electromagnetic radiation to a medical device that converts the processed electromagnetic radiation into an image. The plurality of fiber optic cable transfer brackets 104 transfers the exchange of electromagnetic radiation between the disposable catheter cable structure 101, the disposable catheter terminating structure 102, and the permanent catheter terminal 103.

The disposable catheter cable structure 101 forms the working element of an endoscope. The disposable catheter cable structure 101 forms the structure of the endoscope that transmits electromagnetic radiation into a patient that illuminates a field of illumination within the patient. The disposable catheter cable structure 101 captures electromagnetic radiation from within a field of view that is within the patient. The field of view of the disposable catheter cable structure 101 is contained within the field of illumination that is illuminated by the disposable catheter cable structure 101.

The disposable catheter cable structure 101 transports the captured electromagnetic radiation to the disposable catheter cable terminating structure 102. The disposable catheter cable structure 101 is a disposable structure. The disposable catheter cable structure 101 is intended for a single use.

The disposable catheter cable structure 101 comprises a first fiber optic illumination cable 111, a second fiber optic illumination cable 112, a first fiber optic image capture cable 113, a second fiber optic image capture cable 114, and a catheter cap 115.

The first fiber optic illumination cable 111 is a fiber optic cable. The first fiber optic illumination cable 111 transmits electromagnetic radiation received from the disposable catheter cable terminating structure 102 to the field of illumination.

The second fiber optic illumination cable 112 is a fiber optic cable. The second fiber optic illumination cable 112 transmits electromagnetic radiation received from the disposable catheter cable terminating structure 102 to the field of illumination.

The first fiber optic image capture cable 113 is a fiber optic cable. The first fiber optic image capture cable 113 transmits electromagnetic radiation captured from the field of view of the disposable catheter cable structure 101 to the disposable catheter cable terminating structure 102.

The second fiber optic image capture cable 114 is a fiber optic cable. The second fiber optic image capture cable 114 transmits electromagnetic radiation captured from the field of view of the disposable catheter cable structure 101 to the disposable catheter cable terminating structure 102.

The catheter cap 115 is a mechanical structure that is positioned on the distal end of the catheter cable that is inserted into the patient. The catheter cap 115 holds the free ends of the first fiber optic illumination cable 111, the second fiber optic illumination cable 112, the first fiber optic image capture cable 113, and the second fiber optic image capture cable 114 in fixed positions relative to each other.

The disposable catheter cable terminating structure 102 is a transfer structure. The disposable catheter cable terminating structure 102 makes the physical connection necessary to transfer electromagnetic radiation between disposable catheter cable structure 101 and the permanent catheter terminal 103. The disposable catheter cable terminating structure 102 transfers electromagnetic radiation received from the permanent catheter terminal 103 into the disposable catheter cable structure 101. The disposable catheter cable terminating structure 102 transfers electromagnetic radiation received from the disposable catheter cable structure 101 into the permanent catheter terminal 103.

The disposable catheter cable terminating structure 102 is a disposable structure. The disposable catheter cable terminating structure 102 is intended for a single use. The physical attachment between the disposable catheter cable terminating structure 102 and the permanent catheter terminal is detachable. The disposable catheter cable terminating structure 102 comprises a disposable housing structure 121 and a cable latch 122.

The disposable housing structure 121 is a rigid structure. The disposable housing structure 121 forms the exterior surfaces of the disposable catheter cable terminating structure 102. The disposable housing structure 121 forms a housing that encloses the first fiber optic cable transfer bracket 141, the second fiber optic cable transfer bracket 142, the third fiber optic cable transfer bracket 143, and the fourth fiber optic cable transfer bracket 144. The disposable housing structure 121 is formed with all the form factors and apertures necessary to allow for the use of the invention 100. The disposable housing structure 121 further comprises an exterior shell 151, a leading channel 152, and a plurality of auxiliary channels 153.

The exterior shell 151 is a rigid structure. The exterior shell 151 is a tubular structure. The exterior shell 151 forms the exterior surfaces of the disposable housing structure 121. The exterior shell 151 is formed with all the form factors and apertures necessary to allow for the use of the invention 100.

The leading channel 152 is a channel that is formed through the exterior shell 151. The leading channel 152 forms a path into the patient. The leading channel 152 forms a structure that allows the user to insert a lead catheter into the patient during use of the disposable catheter cable structure 101 with the patient.

Each auxiliary channel selected from the plurality of auxiliary channels 153 is a channel that is formed through the disposable catheter cable terminating structure 102. Each auxiliary channel selected from the plurality of auxiliary channels 153 forms a pluggable structure that allows for the transfer of material between the disposable catheter cable terminating structure 102 and the permanent catheter terminal 103.

As a first example of the use of the plurality of auxiliary channels 153, an auxiliary channel selected from the plurality of auxiliary channels 153 can be dedicated to receiving a saline solution from the permanent catheter terminal 103 and transferring the saline solution through the disposable catheter cable terminating structure 102 and the disposable catheter cable structure 101 into a patient.

As a second example of use of the plurality of auxiliary channels 153, a vacuum can be applied to an auxiliary channel selected from the plurality of auxiliary channels 153. The applied vacuum generates a suction that allows biological material to be drawn from the patient, through the disposable catheter cable structure 101 and the disposable catheter cable terminating structure 102 into the permanent catheter terminal 103.

Each auxiliary channel selected from the plurality of auxiliary channels 153 forms a channel that allows for the insertion of fluids and additional catheters into the patient during the use of the invention 100. Each individual fiber optic cable transfer brackets selected from the plurality of fiber optic cable transfer brackets 104 is a rigid structure.

The cable latch 122 is a mechanical structure. The cable latch 122 is a spring-loaded structure.

The cable latch 122 mechanically interacts with the first fiber optic cable transfer bracket 141 and the fifth fiber optic cable transfer bracket 145. The cable latch 122 maintains the fifth fiber optic cable transfer bracket 145 in a fixed position relative to the first fiber optic cable transfer bracket 141. The cable latch 122 ensures that the first fiber optic link cable 131 is, and remains, properly aligned with the first fiber optic illumination cable 111.

The cable latch 122 mechanically interacts with the second fiber optic cable transfer bracket 142 and the sixth fiber optic cable transfer bracket 146. The cable latch 122 maintains the sixth fiber optic cable transfer bracket 146 in a fixed position relative to the second fiber optic cable transfer bracket 142. The cable latch 122 ensures that the second fiber optic link cable 132 is, and remains, properly aligned with the second fiber optic illumination cable 112.

The cable latch 122 mechanically interacts with the third fiber optic cable transfer bracket 143 and the seventh fiber optic cable transfer bracket 147. The cable latch 122 maintains the seventh fiber optic cable transfer bracket 147 in a fixed position relative to the third fiber optic cable transfer bracket 143. The cable latch 122 ensures that the third fiber optic link cable 133 is, and remains, properly aligned with the first fiber optic image capture cable 113.

The cable latch 122 mechanically interacts with the fourth fiber optic cable transfer bracket 144 and the eighth fiber optic cable transfer bracket 148. The cable latch 122 maintains the eighth fiber optic cable transfer bracket 148 in a fixed position relative to the fourth fiber optic cable transfer bracket 144. The cable latch 122 ensures that the fourth fiber optic link cable 134 is, and remains, properly aligned with the second fiber optic image capture cable 114.

The permanent catheter terminal 103 is a transfer structure. The permanent catheter terminal 103 makes the physical connection necessary to transfer electromagnetic radiation between disposable catheter cable terminating structure

102 and a medical imaging device. The permanent catheter terminal 103 transfers electromagnetic radiation received from the medical imaging device to the disposable catheter cable terminating structure 102. The permanent catheter terminal 103 transfers electromagnetic radiation received from the disposable catheter cable terminating structure 102 to the medical imaging device. The permanent catheter terminal 103 comprises a first fiber optic link cable 131, a second fiber optic link cable 132, a third fiber optic link cable 133, a fourth fiber optic link cable 134, and a permanent housing structure 135.

The first fiber optic link cable 131 is a fiber optic cable. The first fiber optic link cable 131 transmits electromagnetic radiation received from the medical imaging device to the first fiber optic illumination cable 111.

The second fiber optic link cable 132 is a fiber optic cable. The second fiber optic link cable 132 transmits electromagnetic radiation received from the medical imaging device to the second fiber optic illumination cable 112.

The third fiber optic link cable 133 is a fiber optic cable. The third fiber optic link cable 133 transmits electromagnetic radiation received from the first fiber optic image capture cable 113 to the medical imaging device.

The fourth fiber optic link cable 134 is a fiber optic cable. The fourth fiber optic link cable 134 transmits electromagnetic radiation received from the second fiber optic image capture cable 114 to the medical imaging device.

The permanent housing structure 135 is a rigid structure. The permanent housing structure 135 forms the exterior surfaces of the permanent catheter terminal 103. The permanent housing structure 135 forms a housing that encloses the fifth fiber optic cable transfer bracket 145, the sixth fiber optic cable transfer bracket 146, the seventh fiber optic cable transfer bracket 147, and the eighth fiber optic cable transfer bracket 148. The permanent housing structure 135 is formed with all the form factors and apertures necessary to allow for the use of the invention 100.

Each individual cable transfer bracket 161 selected from the plurality of fiber optic cable transfer brackets 104 is a transfer structure. Any individual cable transfer bracket 161 initially selected from the plurality of fiber optic cable transfer brackets 104 removably attaches to an individual cable transfer bracket 161 subsequently selected from the plurality of fiber optic cable transfer brackets 104. The initially selected individual cable transfer bracket 161 and the subsequently selected individual cable transfer bracket 161 forms a structure that transfers electromagnetic radiation between the disposable catheter cable terminating structure 102 and the permanent catheter terminal 103.

The individual cable transfer bracket 161 initially selected from the plurality of fiber optic cable transfer brackets 104 and the individual cable transfer bracket 161 subsequently selected from the plurality of fiber optic cable are detachably attached to each other to form a pluggable connection. The pluggable connection formed by the initially selected individual cable transfer bracket 161 and the subsequently selected individual cable transfer bracket 161 forms the physical transfer structure that transfers the electromagnetic radiation between the disposable catheter cable terminating structure 102 and the permanent catheter terminal 103.

Each selected individual cable transfer bracket 161 is a tubular structure. Each selected individual cable transfer bracket 161 maintains a protected space that protects the fiber optic cable associated with the selected individual cable transfer bracket 161. Each individual transfer bracket 161 comprises a cable mount 162 and a securing spring 163.

The cable mount 162 of each selected individual cable transfer bracket 161 is a plate like structure. The cable mount 162 maintains the fiber optic cable associated with the cable mount 162 in a fixed position within the protected space formed by the selected individual cable transfer bracket 161.

The securing spring 163 is an energy storage device. The securing spring 163 is deformed into a compressed position when the fiber optic cable associated with the selected individual cable transfer bracket 161 is inserted into the selected individual cable transfer bracket 161. The securing spring 163 maintains a pressure against the cable mount 162 that holds the selected individual cable transfer bracket 161 in a fixed position.

The plurality of fiber optic cable transfer brackets 104 comprises a first fiber optic cable transfer bracket 141, a second fiber optic cable transfer bracket 142, a third fiber optic cable transfer bracket 143, a fourth fiber optic cable transfer bracket 144, a fifth fiber optic cable transfer bracket 145, a sixth fiber optic cable transfer bracket 146, a seventh fiber optic cable transfer bracket 147, and an eighth fiber optic cable transfer bracket 148.

The first fiber optic cable transfer bracket 141 mounts in the disposable housing structure 121. The first fiber optic cable transfer bracket 141 is a bracket that secures the first fiber optic illumination cable 111 in a fixed position relative within the disposable housing structure 121 of the disposable catheter cable terminating structure 102.

The second fiber optic cable transfer bracket 142 mounts in the disposable housing structure 121. The second fiber optic cable transfer bracket 142 is a bracket that secures the second fiber optic illumination cable 112 in a fixed position relative within the disposable housing structure 121 of the disposable catheter cable terminating structure 102.

The third fiber optic cable transfer bracket 143 mounts in the disposable housing structure 121. The third fiber optic cable transfer bracket 143 is a bracket that secures the first fiber optic image capture cable 113 in a fixed position relative within the disposable housing structure 121 of the disposable catheter cable terminating structure 102.

The fourth fiber optic cable transfer bracket 144 mounts in the disposable housing structure 121. The fourth fiber optic cable transfer bracket 144 is a bracket that secures the second fiber optic image capture cable 114 in a fixed position relative within the disposable housing structure 121 of the disposable catheter cable terminating structure 102.

The fifth fiber optic cable transfer bracket 145 mounts in the permanent housing structure 135. The fifth fiber optic cable transfer bracket 145 is a bracket that secures the first fiber optic link cable 131 in a fixed position relative within the permanent housing structure 135 of the permanent catheter terminal 103.

The sixth fiber optic cable transfer bracket 146 mounts in the permanent housing structure 135. The sixth fiber optic cable transfer bracket 146 is a bracket that secures the second fiber optic link cable 132 in a fixed position relative within the permanent housing structure 135 of the permanent catheter terminal 103.

The seventh fiber optic cable transfer bracket 147 mounts in the permanent housing structure 135. The seventh fiber optic cable transfer bracket 147 is a bracket that secures the third fiber optic link cable 133 in a fixed position relative within the permanent housing structure 135 of the permanent catheter terminal 103.

The eighth fiber optic cable transfer bracket 148 mounts in the permanent housing structure 135. The eighth fiber optic cable transfer bracket 148 is a bracket that secures the fourth fiber optic link cable 134 in a fixed position relative within the permanent housing structure 135 of the permanent catheter terminal 103.

The first fiber optic illumination cable 111 is secured within the first fiber optic cable transfer bracket 141. The second fiber optic illumination cable 112 is secured within the second fiber optic cable transfer bracket 142. The first fiber optic image capture cable 113 is secured within the third fiber optic cable transfer bracket 143. The second fiber optic image capture cable 114 is secured within the fourth fiber optic cable transfer bracket 144. The first fiber optic link cable 131 is secured within the fifth fiber optic cable transfer bracket 145. The second fiber optic link cable 132 is secured within the sixth fiber optic cable transfer bracket 146. The third fiber optic link cable 133 is secured within the seventh fiber optic cable transfer bracket 147. The fourth fiber optic link cable is secured within the eighth fiber optic cable transfer bracket 148.

The fifth fiber optic cable transfer bracket 145 attaches to the first fiber optic cable transfer bracket 141 such that the illuminating electromagnetic radiation generated by the medical device is transferred from the first fiber optic link cable 131 to the first fiber optic illumination cable 111. The sixth fiber optic cable transfer bracket 146 attaches to the second fiber optic cable transfer bracket 142 such that the illuminating electromagnetic radiation generated by the medical device is transferred from the second fiber optic link cable 132 to the second fiber optic illumination cable 112.

The seventh fiber optic cable transfer bracket 147 attaches to the third fiber optic cable transfer bracket 143 such that the electromagnetic radiation captured from the field of illumination by the first fiber optic image capture cable 113 is transferred to the medical device through the third fiber optic link cable 133. The eighth fiber optic cable transfer bracket attaches to the fourth fiber optic cable transfer bracket 144 such that the electromagnetic radiation captured from the field of illumination by the second fiber optic image capture cable 114 is transferred to the medical device through the fourth fiber optic link cable 134.

The following definitions were used in this disclosure:

Align: As used in this disclosure, align refers to an arrangement of objects that are: 1) arranged in a straight plane or line; 2) arranged to give a directional sense of a plurality of parallel planes or lines; or, 3) a first line or curve is congruent to and overlaid on a second line or curve.

Barrier: As used in this disclosure, a barrier is a physical obstacle that forms a boundary between a first space and a second space. The barrier prevents the passage of an object between the first space and the second space.

Cant: As used in this disclosure, a cant is an angular deviation from one or more reference lines (or planes) such as a vertical line (or plane) or a horizontal line (or plane).

Cap: As used in this disclosure, a cap is a protective structure that encloses a space, opening, or fitting.

Catheter: As used in this disclosure, a catheter is a flexible tube that is inserted into the body through which images may be captured and fluids may be introduced into or removed from the body. Endoscope is a synonym for catheter. A condom catheter is a tubular structure that is designed be worn over the penis of a patient. The condom catheter transports captured excretions away from the penis of the patient.

Center: As used in this disclosure, a center is a point that is: 1) the point within a circle that is equidistant from all the points of the circumference; 2) the point within a regular polygon that is equidistant from all the vertices of the regular polygon; 3) the point on a line that is equidistant from the ends of the line; 4) the point, pivot, or axis around which something revolves; or, 5) the centroid or first moment of an area or structure. In cases where the appropriate definition or definitions are not obvious, the fifth option should be used in interpreting the specification.

Center Axis: As used in this disclosure, the center axis is the axis of a cylinder or a prism. The center axis of a prism is the line that joins the center point of the first congruent face of the prism to the center point of the second corresponding congruent face of the prism. The center axis of a pyramid refers to a line formed through the apex of the pyramid that is perpendicular to the base of the pyramid. When the center axes of two cylinder, prism or pyramidal structures share the same line they are said to be aligned. When the center axes of two cylinder, prism or pyramidal structures do not share the same line they are said to be offset.

Channel: As used in this disclosure, a channel is a negative space used to guide the motion of an object or through which an object or fluid passes.

Composite Prism: As used in this disclosure, a composite prism refers to a structure that is formed from a plurality of structures selected from the group consisting of a prism structure and a pyramid structure. The plurality of selected structures may or may not be truncated. The plurality of prism structures are joined together such that the center axes of each of the plurality of structures are aligned. The congruent ends of any two structures selected from the group consisting of a prism structure and a pyramid structure need not be geometrically similar.

Congruent: As used in this disclosure, congruent is a term that compares a first object to a second object. Specifically, two objects are said to be congruent when: 1) they are geometrically similar; and, 2) the first object can superimpose over the second object such that the first object aligns, within manufacturing tolerances, with the second object.

Correspond: As used in this disclosure, the term correspond is used as a comparison between two or more objects wherein one or more properties shared by the two or more objects match, agree, or align within acceptable manufacturing tolerances.

Disk: As used in this disclosure, a disk is a prism-shaped object that is flat in appearance. The disk is formed from two congruent ends that are attached by a lateral face. The sum of the surface areas of two congruent ends of the prism-shaped object that forms the disk is greater than the surface area of the lateral face of the prism-shaped object that forms the disk.

In this disclosure, the congruent ends of the prism-shaped structure that forms the disk are referred to as the faces of the disk.

Disposable: As used in this disclosure, disposable is an adjective that refers to an object that is designed and intended for a single use. Within this context, an object would be considered disposable if it is not reusable after its initial use.

Environment: As used in this disclosure, an environment refers to the physical conditions surrounding an object. The term environment is often limited to the physical conditions that the object interacts with.

Exterior: As used in this disclosure, the exterior is used as a relational term that implies that an object is not contained within the boundary of a structure or a space.

Field of Illumination: As used in this disclosure, a field of illumination refers to an area illuminated by electromagnetic radiation projected from an electrical device such as a lamp or transmission antenna.

Field of View: As used in this disclosure, a field of view refers to one or more angles which delimits an area from which electromagnetic radiation will be sensed by a person or an image sensor.

Form Factor: As used in this disclosure, the term form factor refers to the size and shape of an object.

Geometrically Similar: As used in this disclosure, geometrically similar is a term that compares a first object to a second object wherein: 1) the sides of the first object have a one to one correspondence to the sides of the second object; 2) wherein the ratio of the length of each pair of corresponding sides are equal; 3) the angles formed by the first object have a one to one correspondence to the angles of the second object; and, 4) wherein the corresponding angles are equal. The term geometrically identical refers to a situation where the ratio of the length of each pair of corresponding sides equals 1. By the term essentially geometrically similar is meant that the primary shapes of two objects are geometrically similar except that there are functional items (such as fastening devices) associated with the primary shape may not maintain the ratio for geometric similarity. By the term roughly geometrically similar is meant that the form factors between the primary shape of the two objects can vary by a factor of up to 10% when the two objects are normalized to be roughly geometrically identical.

Housing: As used in this disclosure, a housing is a rigid structure that encloses and protects one or more devices.

Image: As used in this disclosure, an image is an optical representation or reproduction of an indicia or of the appearance of something or someone.

Interior: As used in this disclosure, the interior is used as a relational term that implies that an object is contained within the boundary of a structure or a space.

Negative Space: As used in this disclosure, negative space is a method of defining an object through the use of open or empty space as the definition of the object itself, or, through the use of open or empty space to describe the boundaries of an object.

Offset Composite Prism: As used in this disclosure, an offset composite prism structure is a non-Euclidean structure. The shape of the offset composite prism structure is reasonably approximated by a plurality of prism structures. The shape of the offset composite prism structure is formed by joining the congruent end of a first prism structure is joined to the congruent end of a second structure such that the center axis of the first prism structure forms a cant with the center axis of the second prism structure.

One to One: When used in this disclosure, a one to one relationship means that a first element selected from a first set is in some manner connected to only one element of a second set. A one to one correspondence means that the one to one relationship exists both from the first set to the second set and from the second set to the first set. A one to one fashion means that the one to one relationship exists in only one direction.

Pan: As used in this disclosure, a pan is a hollow and prism-shaped containment structure. The pan has a single open face. The open face of the pan is often, but not always, the superior face of the pan. The open face is a surface selected from the group consisting of: a) a congruent end of the prism structure that forms the pan; and, b) a lateral face of the prism structure that forms the pan. A semi-enclosed pan refers to a pan wherein the closed end of prism structure of the pan and/or a portion of the closed lateral faces of the pan are open.

Perimeter: As used in this disclosure, a perimeter is one or more curved or straight lines that bounds an enclosed area on a plane or surface. The perimeter of a circle is commonly referred to as a circumference.

Primary Shape: As used in this disclosure, the primary shape refers to a description of the rough overall geometric shape of an object that is assembled from multiple components or surfaces. Use Roughly Primary Structure: As used in this disclosure, a primary structure refers to the component of an object that the other components attach to. The primary structure is also called the base structure.

Prism: As used in this disclosure, a prism is a three-dimensional geometric structure wherein: 1) the form factor of two faces of the prism are congruent; and, 2) the two congruent faces are parallel to each other. The two congruent faces are 16 also commonly referred to as the ends of the prism. The surfaces that connect the two congruent faces are called the lateral faces. In this disclosure, when further description is required a prism will be named for the geometric or descriptive name of the form factor of the two congruent faces. If the form factor of the two corresponding faces has no clearly established or well-known geometric or descriptive name, the term irregular prism will be used. The center axis of a prism is defined as a line that joins the center point of the first congruent face of the prism to the center point of the second corresponding congruent face of the prism. The center axis of a prism is otherwise analogous to the center axis of a cylinder. A prism wherein the ends are circles is commonly referred to as a cylinder.

Protected Space: As used in this disclosure, a protected space is a negative space within which an object is stored. The protected space is enclosed by a barrier structure that: a) prevents damage to the object contained within the protected space; b) maintains conditions that are appropriate for the object; c) protects the object within the protected space from potential dangers that are outside of the protected space; or, d) maintains the privacy of the object within the protected space.

Rigid Structure: As used in this disclosure, a rigid structure is a solid structure formed from an inelastic material that resists changes in shape. A rigid structure will permanently deform as it fails under a force. See bimodal flexible structure.

Semi-Rigid Structure: As used in this disclosure, a semi-rigid structure is a solid structure that is stiff but not wholly inflexible and that will deform under force before breaking. A semi-rigid structure may or may not behave with an elastic nature in that a semi-rigid structure need not return to its relaxed shape.

Sensor: As used in this disclosure, a sensor is a device that receives and responds in a predetermined way to a signal or stimulus. As further used in this disclosure, a threshold sensor is a sensor that generates a signal that indicates whether the signal or stimulus is above or below a given threshold for the signal or stimulus.

Suction: As used in this disclosure, suction refers to the generation of a vacuum that is used to transport a fluid.

Tool: As used in this disclosure, a tool is a device, an apparatus, or an instrument that is used to carry out an activity, operation, or procedure. A tool generally comprises a working element and a handle. The handle of a tool that forms a sub-component of a larger structure is referred to as a mount.

Tube: As used in this disclosure, a tube is a hollow prism-shaped device formed with two open congruent ends. The tube is used for transporting liquids (including bulk solids) and gases. The line that connects the center of the first congruent face of the prism to the center of the second congruent face of the prism is referred to as the center axis of the tube or the centerline of the tube. When two tubes share the same centerline they are said to be aligned. When the centerlines of two tubes are perpendicular to each other, the tubes are said to be perpendicular to each other. In this disclosure, the terms inner dimensions of a tube and outer dimensions of a tube are used as they would be used by those skilled in the plumbing arts.

Vacuum: As used in this disclosure, vacuum is used to describe a first space that contains gas at a reduced gas pressure relative to the gas pressure of a second space. If the first space and the second space are connected together, this pressure differential will cause gas from the second space to move towards the first space until the pressure differential is eliminated.

Working Element: As used in this disclosure, the working element of a tool is the physical element on the tool that performs the actual activity, operation, or procedure the tool is designed to perform. For example, the cutting edge of a blade is the working element of a knife.

With respect to the above description, it is to be realized that the optimum dimensional relationship for the various components of the invention described above and in FIGS. 1 through 23 include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

The inventor claims:

1. A disposable endoscope comprising:
a disposable catheter cable structure, a disposable catheter terminating structure, a permanent catheter terminal, and a plurality of fiber optic cable transfer brackets;
wherein the disposable catheter cable structure connects to the disposable catheter terminating structure;
wherein the disposable catheter terminating structure connects to the permanent catheter terminal;
wherein each fiber optic cable transfer bracket mounts in a structure selected from the group consisting of: a) the disposable catheter terminating structure; and, b) the permanent catheter terminal;
wherein any individual cable transfer bracket initially selected from the plurality of fiber optic cable transfer brackets removably attaches to an individual cable transfer bracket subsequently selected from the plurality of fiber optic cable transfer brackets;
wherein the initially selected individual cable transfer bracket and the subsequently selected individual cable transfer bracket forms a physical structure that transfers electromagnetic radiation between the disposable catheter cable terminating structure and the permanent catheter terminal;
wherein the initially selected individual cable transfer bracket and the subsequently selected individual cable transfer bracket are detachably attached to each other;

wherein each selected individual cable transfer bracket maintains a protected space that protects a fiber optic cable associated with the selected individual cable transfer bracket;

wherein each individual transfer bracket comprises a cable mount and a securing spring;

wherein the cable mount maintains a fiber optic cable associated with the cable mount in a fixed position within the protected space formed by the selected individual cable transfer bracket;

wherein the securing spring is deformed into a compressed position when the fiber optic cable associated with the selected individual cable transfer bracket is inserted into the selected individual cable transfer bracket;

wherein the securing spring maintains a pressure against the cable mount that holds the selected individual cable transfer bracket in a fixed position.

2. The disposable endoscope according to claim 1 wherein the disposable catheter cable structure is a fiber optic device that: a) generates a field of illumination within a patient; b) captures electromagnetic radiation from within a field of view; and, c) transmits the electromagnetic radiation to the disposable catheter terminating structure;

wherein the disposable catheter terminating structure is a signal transfer structure;

wherein the disposable catheter terminating structure: a) receives the electromagnetic radiation transmitted by the disposable catheter cable structure; and, b) transfers the received electromagnetic radiation to the permanent catheter terminal;

wherein the permanent catheter terminal subsequently transfers the received electromagnetic radiation to a medical device that converts the processed electromagnetic radiation into an image;

wherein the plurality of fiber optic cable transfer brackets transfers the electromagnetic radiation between the disposable catheter cable structure, the disposable catheter terminating structure, and the permanent catheter terminal.

3. The disposable endoscope according to claim 2 wherein the disposable catheter cable structure forms a working element of an endoscope;

wherein the disposable catheter cable structure forms the structure of the disposable endoscope that transmits electromagnetic radiation into a patient that illuminates the field of illumination within the patient;

wherein the disposable catheter cable structure captures electromagnetic radiation from within the field of view that is within the patient;

wherein the field of view of the disposable catheter cable structure is contained within the field of illumination that is illuminated by the disposable catheter cable structure;

wherein the disposable catheter cable structure transports the captured electromagnetic radiation to the disposable catheter cable terminating structure;

wherein the disposable catheter cable structure is a disposable structure;

wherein the disposable catheter cable structure is intended for a single use.

4. The disposable endoscope according to claim 3 wherein a disposable housing structure further comprises a leading channel and a plurality of auxiliary channels;

wherein the leading channel is a structure that allows a user to insert a catheter;

wherein each of the plurality of auxiliary channels forms a pluggable structure that allows for transfer of material between the disposable catheter cable terminating structure and the permanent catheter terminal.

5. The disposable endoscope according to claim 4 wherein the disposable catheter cable terminating structure is a transfer structure;

wherein the disposable catheter cable terminating structure makes a physical connection necessary to transfer electromagnetic radiation between the disposable catheter cable structure and the permanent catheter terminal;

wherein the disposable catheter cable terminating structure transfers electromagnetic radiation received from the permanent catheter terminal into the disposable catheter cable structure;

wherein the disposable catheter cable terminating structure transfers electromagnetic radiation received from the disposable catheter cable structure into the permanent catheter terminal;

wherein the disposable catheter cable terminating structure is a disposable structure;

wherein the disposable catheter cable terminating structure is intended for a single use;

wherein a physical attachment between the disposable catheter cable terminating structure and the permanent catheter terminal is detachable.

6. The disposable endoscope according to claim 5 wherein the permanent catheter terminal is a transfer structure;

wherein the permanent catheter terminal makes a physical connection necessary to transfer electromagnetic radiation between the disposable catheter cable terminating structure and a medical imaging device;

wherein the permanent catheter terminal transfers electromagnetic radiation received from the medical imaging device to the disposable catheter cable terminating structure;

wherein the permanent catheter terminal transfers electromagnetic radiation received from the disposable catheter cable terminating structure to the medical imaging device.

7. The disposable endoscope according to claim 6 wherein the permanent catheter terminal comprises a first fiber optic link cable, a second fiber optic link cable, a third fiber optic link cable, a fourth fiber optic link cable, and a permanent housing structure;

wherein the first fiber optic link cable is a fiber optic cable;

wherein the first fiber optic link cable transmits electromagnetic radiation received from the medical imaging device to a first fiber optic illumination cable;

wherein the second fiber optic link cable is a fiber optic cable;

wherein the second fiber optic link cable transmits electromagnetic radiation received from the medical imaging device to a second fiber optic illumination cable;

wherein the third fiber optic link cable is a fiber optic cable;

wherein the third fiber optic link cable transmits electromagnetic radiation received from a first fiber optic image capture cable to the medical imaging device;

wherein the fourth fiber optic link cable is a fiber optic cable;

wherein the fourth fiber optic link cable transmits electromagnetic radiation received from a second fiber optic image capture cable to the medical imaging device;

wherein the permanent housing structure is a rigid structure;

wherein the permanent housing structure forms exterior surfaces of the permanent catheter terminal.

8. The disposable endoscope according to claim 7 wherein each individual cable transfer bracket selected from the plurality of fiber optic cable transfer brackets is a transfer structure;

wherein each selected individual cable transfer bracket is a tubular structure;

wherein the cable mount of each selected individual cable transfer bracket is a platelike structure;

wherein the securing spring is an energy storage device.

9. The disposable endoscope according to claim 8 wherein the disposable catheter cable structure comprises the first fiber optic illumination cable, the second fiber optic illumination cable, the first fiber optic image capture cable, the second fiber optic image capture cable, and a catheter cap;

wherein the first fiber optic illumination cable is a fiber optic cable;

wherein the first fiber optic illumination cable transmits electromagnetic radiation received from the disposable catheter cable terminating structure to the field of illumination;

wherein the second fiber optic illumination cable is a fiber optic cable;

wherein the second fiber optic illumination cable transmits electromagnetic radiation received from the disposable catheter cable terminating structure to the field of illumination;

wherein the first fiber optic image capture cable is a fiber optic cable;

wherein the first fiber optic image capture cable transmits electromagnetic radiation captured from the field of view of the disposable catheter cable structure to the disposable catheter cable terminating structure;

wherein the second fiber optic image capture cable is a fiber optic cable;

wherein the second fiber optic image capture cable transmits electromagnetic radiation captured from the field of view of the disposable catheter cable structure to the disposable catheter cable terminating structure;

wherein the catheter cap is a mechanical structure that is positioned on a distal end of the catheter cable that is inserted into the patient;

wherein the catheter cap holds free ends of the first fiber optic illumination cable, the second fiber optic illumination cable, the second fiber optic illumination cable, and the second fiber optic image capture cable in fixed positions relative to each other.

10. The disposable endoscope according to claim 9 wherein the disposable catheter cable terminating structure comprises a disposable housing structure and a cable latch;

wherein the disposable housing structure is a rigid structure;

wherein the disposable housing structure forms the exterior surfaces of the disposable catheter cable terminating structure;

wherein the disposable housing structure forms a housing that encloses the first fiber optic cable transfer bracket, the second fiber optic cable transfer bracket, the third fiber optic cable transfer bracket, and the fourth fiber optic cable transfer bracket;

wherein the disposable housing structure is formed with at least one form factor and aperture to allow for the use of the disposable endoscope.

11. The disposable endoscope according to claim 10 wherein the plurality of fiber optic cable transfer brackets comprises a first fiber optic cable transfer bracket, a second fiber optic cable transfer bracket, a third fiber optic cable transfer bracket, a fourth fiber optic cable transfer bracket, a fifth fiber optic cable transfer bracket, a sixth fiber optic cable transfer bracket, a seventh fiber optic cable transfer bracket, and an eighth fiber optic cable transfer bracket;

wherein the first fiber optic cable transfer bracket mounts in the disposable housing structure;

wherein the first fiber optic cable transfer bracket is a bracket that secures the first fiber optic illumination cable in a fixed position relative within the disposable housing structure of the disposable catheter cable terminating structure;

wherein the second fiber optic cable transfer bracket mounts in the disposable housing structure;

wherein the second fiber optic cable transfer bracket is a bracket that secures the second fiber optic illumination cable in a fixed position relative within the disposable housing structure of the disposable catheter cable terminating structure;

wherein the third fiber optic cable transfer bracket mounts in the disposable housing structure;

wherein the third fiber optic cable transfer bracket is a bracket that secures the first fiber optic image capture cable in a fixed position relative within the disposable housing structure of the disposable catheter cable terminating structure;

wherein the fourth fiber optic cable transfer bracket mounts in the disposable housing structure;

wherein the fourth fiber optic cable transfer bracket is a bracket that secures the second fiber optic image capture cable in a fixed position relative within the disposable housing structure of the disposable catheter cable terminating structure;

wherein the fifth fiber optic cable transfer bracket mounts in the permanent housing structure;

wherein the fifth fiber optic cable transfer bracket is a bracket that secures the first fiber optic link cable in a fixed position relative within the permanent housing structure of the permanent catheter terminal;

wherein the sixth fiber optic cable transfer bracket mounts in the permanent housing structure;

wherein the sixth fiber optic cable transfer bracket is a bracket that secures the second fiber optic link cable in a fixed position relative within the permanent housing structure of the permanent catheter terminal;

wherein the seventh fiber optic cable transfer bracket mounts in the permanent housing structure;

wherein the seventh fiber optic cable transfer bracket is a bracket that secures the third fiber optic link cable in a fixed position relative within the permanent housing structure of the permanent catheter terminal;

wherein the eighth fiber optic cable transfer bracket mounts in the permanent housing structure;

wherein the eighth fiber optic cable transfer bracket is a bracket that secures the fourth fiber optic link cable in a fixed position relative within the permanent housing structure of the permanent catheter terminal.

12. The disposable endoscope according to claim 11 wherein the first fiber optic illumination cable is secured within the first fiber optic cable transfer bracket;

wherein the second fiber optic illumination cable is secured within the second fiber optic cable transfer bracket;

wherein the first fiber optic image capture cable is secured within the third fiber optic cable transfer bracket;

wherein the second fiber optic image capture cable is secured within the fourth fiber optic cable transfer bracket;

wherein the first fiber optic link cable is secured within the fifth fiber optic cable transfer bracket;

wherein the second fiber optic link cable is secured within the sixth fiber optic cable transfer bracket;

wherein the third fiber optic link cable is secured within the seventh fiber optic cable transfer bracket;

wherein the fourth fiber optic link cable is secured within the eighth fiber optic cable transfer bracket;

wherein the fifth fiber optic cable transfer bracket attaches to the first fiber optic cable transfer bracket such that the illuminating electromagnetic radiation generated by the medical device is transferred from the first fiber optic link cable to the first fiber optic illumination cable;

wherein the sixth fiber optic cable transfer bracket attaches to the second fiber optic cable transfer bracket such that the illuminating electromagnetic radiation generated by the medical device is transferred from the second fiber optic link cable to the second fiber optic illumination cable;

wherein the seventh fiber optic cable transfer bracket attaches to the third fiber optic cable transfer bracket such that the electromagnetic radiation captured from the field of illumination by the first fiber optic image capture cable is transferred to the medical device through the third fiber optic link cable;

wherein the eighth fiber optic cable transfer bracket attaches to the fourth fiber optic cable transfer bracket such that the electromagnetic radiation captured from the field of illumination by the second fiber optic image capture cable is transferred to the medical device through the fourth fiber optic link cable.

13. The disposable endoscope according to claim 12 wherein the cable latch is a mechanical structure;

wherein the cable latch is a spring-loaded structure;

wherein the cable latch mechanically interacts with the first fiber optic cable transfer bracket and the fifth fiber optic cable transfer bracket;

wherein the cable latch maintains the fifth fiber optic cable transfer bracket in a fixed position relative to the first fiber optic cable transfer bracket;

wherein the cable latch is configured to align the first fiber optic link cable with the first fiber optic illumination cable;

wherein the cable latch mechanically interacts with the second fiber optic cable transfer bracket and the sixth fiber optic cable transfer bracket;

wherein the cable latch maintains the sixth fiber optic cable transfer bracket in a fixed position relative to the second fiber optic cable transfer bracket;

wherein the cable latch is configured to align the second fiber optic link cable with the second fiber optic illumination cable;

wherein the cable latch mechanically interacts with the third fiber optic cable transfer bracket and the seventh fiber optic cable transfer bracket;

wherein the cable latch maintains the seventh fiber optic cable transfer bracket in a fixed position relative to the third fiber optic cable transfer bracket;

wherein the cable latch is configured to align the third fiber optic link cable with the first fiber optic image capture cable;

wherein the cable latch mechanically interacts with the fourth fiber optic cable transfer bracket and the eighth fiber optic cable transfer bracket;

wherein the cable latch maintains the eighth fiber optic cable transfer bracket in a fixed position relative to the fourth fiber optic cable transfer bracket;

wherein the cable latch is configured to align the fourth fiber optic link cable with the second fiber optic image capture cable.

14. The disposable endoscope according to claim 4 wherein an auxiliary channel selected from the plurality of auxiliary channels is dedicated to receiving a saline solution from the permanent catheter terminal and configured to be transferring the saline solution through the disposable catheter cable terminating structure and the disposable catheter cable structure into a patient.

15. The disposable endoscope according to claim 14 wherein an auxiliary channel selected from the plurality of auxiliary channels involves a vacuum that generates a suction that allows biological material to be configured to be drawn from the patient, through the disposable catheter cable structure and the disposable catheter cable terminating structure into the permanent catheter terminal.

16. The disposable endoscope according to claim 14 wherein an auxiliary channel selected from the plurality of auxiliary channels forms a channel that is configured to allow for the insertion of fluids and additional catheters into the patient during use.

* * * * *